United States Patent [19]

Boyer et al.

[11] Patent Number: 4,605,768

[45] Date of Patent: Aug. 12, 1986

[54] 1-CYCLOALKYLAMINO-3-T-BUTYLAMINO-2-PROPANOLS, A METHOD OF PREPARING THE SAME, AND A METHOD OF USE THEREOF

[75] Inventors: Chantal Boyer, Le Pian Medoc; Jean C. Colleter, Blanquefort; Marie-Helene Creuzet, Bordeaux; Claude Feniou, Pessac; Michel Laguerre, Gradignan; Henri Pontagnier, Pessac; Gisele Prat, Talence, all of France

[73] Assignee: Societe Cortial, Paris, France

[21] Appl. No.: 684,949

[22] Filed: Dec. 21, 1984

[30] Foreign Application Priority Data

Dec. 22, 1983 [FR] France .................... 83 20748

[51] Int. Cl.$^4$ .................... C07C 87/32; C07C 87/45
[52] U.S. Cl. ............................ 564/461; 564/454
[58] Field of Search ............. 564/461, 503, 454

[56] References Cited

U.S. PATENT DOCUMENTS 2,937,185  5/1960  Biel .................................. 564/503

OTHER PUBLICATIONS

Dantschev et al "Synthese und Pharmokologische Untersuchung von N-Substituierten Derivaten des 1-Cycloalkoxy-3-Amino-2-Propanols" in *Archiv der Pharmazie*, No. 7, Band 312, Jul. 1979, pp. 857-863 (& abstract).

Gaertner, V. R. "Ring Opening Nucleophilic Alkylations by Tertiary Azetidines" in *J. of Heterocyclic Chemistry*, vol. 6, No. 3 Jun. 1969, pp. 273-277.

*Primary Examiner*—Charles F. Warren
*Assistant Examiner*—John A. Sopp
*Attorney, Agent, or Firm*—Oblon, Fisher, Spivak, McClelland & Maier

[57] ABSTRACT

A compound having the formula:

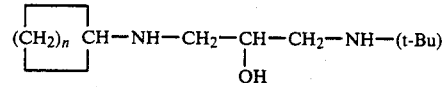

wherein n is an integer between 6 and 11, inclusive; or the pharmaceutically-acceptable salts thereof.

The compounds of the present invention and compositions containing the same are useful as antimicrobial agents in the disinfection of healthy or injured skin or mucous or serous membranes.

7 Claims, No Drawings

1-CYCLOALKYLAMINO-3-T-BUTYLAMINO-2-PROPANOLS, A METHOD OF PREPARING THE SAME, AND A METHOD OF USE THEREOF

BACKGROUND OF THE INVENTION

1. Field of the Invention

The present invention relates to 1-cycloalkylamino-3-t-butylamino-2-propanols, and the preparation and use of these compounds.

2. Description of the Prior Art

Compounds having the general formula:

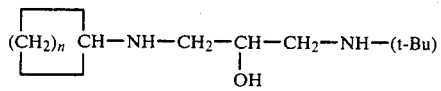

are unknown, except for the case where the cyclic moiety is a cyclohexyl group, i.e., where n=5 in the above formula. This compound was synthesized in a study of nucleophilic decyclizing alkylations by tertiary azetidines. Gaertner, V. R., 1969, *J. Heterocyclic Chem.*, 6(3):273-7. However, no application or use of this compound is known other than in the study of the above-described alkylation reactions.

While there are several general classes of antimicrobial agents, many of these antimicrobial agents are also highly irritating or toxic. For example, some such agents even product temporary allergic skin reactions. Hence, a need clearly exists for an antimicrobial agent which has a high antimicrobial activity, but which has a relatively low toxicity toward humans and animals.

SUMMARY OF THE INVENTION

Accordingly, it is an object of the present invention to provide antimicrobial compounds which have a high antimicrobial activity, but which have a relatively low toxicity toward humans and animals.

It is also an object of this invention to provide antimicrobial compositions which are advantageously employed as antiseptics or disinfectants for injured or healthy skin or mucous or serous membranes, and for the disinfection of materials and surfaces.

Moreover, it is also an object of the present invention to provide a process for preparing the antimicrobial compounds of the present invention.

Further, it is also an object of this invention to provide a process for effecting antisepsis of skin, or mucous or serous membranes.

It is also an object of the present invention to provide a process for disinfecting materials and surfaces thereof.

According to the present invention, the foregoing and other objects are attained by providing a compound having the formula:

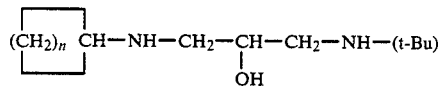

wherein n is an integer between 6 and 11 inclusive, or the pharmaceutically acceptable salts thereof.

DETAILED DESCRIPTION OF THE PREFERRED EMBODIMENTS

According to the present invention, it has now been found that compounds having the general formula (I):

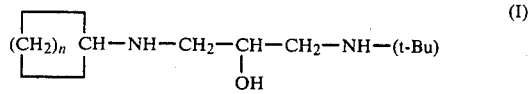

exhibit antimicrobial properties as well as having an anti-aggregant action upon blood platelets.

The compounds of the present invention can be prepared by, first, reacting an amine compound of the formula:

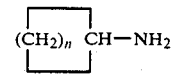

wherein n is an integer between 6 and 11 inclusive, with epichlorohydrin in an organic solvent at the boiling point of the solvent, i.e., at reflux. Particularly useful organic solvents are the absolute lower alkyl alcohols such as methyl, ethyl, n-propyl and isopropyl alcohol. In particular, the use of absolute ethyl alcohol at reflux is especially preferred. Then, the product obtained from this first reaction, having the formula:

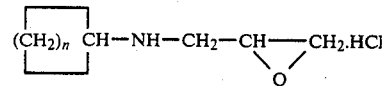

is reacted with t-butylamine in an organic solvent at the boiling point of the solvent, i.e., at reflux. Particularly useful organic solvents are the absolute lower alkyl alcohols such absolute methyl, ethyl, n-propyl and iso-propyl alcohols. In particular, the use of absolute ethyl alcohol of reflux is especially preferred. Thereby, compounds having the formula (I) are produced.

It is preferred, in the first stage of the reaction, to react approximately equimolar amounts of the cyclic amine with the epichlorohydrin, i.e., about 0.75 to 1.25 moles of epichlorohydrin per mole of cyclic amine. More preferred, however, is the use of about 1.1 moles of epichlorohydrin per mole of cyclic amine. In particular, it should be noted that the cyclic amines which are particularly contemplated are cycloheptyl ($C_7$) amine, cyclooctyl ($C_8$) amine, cyclononyl ($C_9$) amine, cyclodecyl ($C_{10}$) amine, cycloundecyl ($C_{11}$) amine and cyclododecyl ($C_{12}$) amine. However, particularly preferred is the use of cyclooctyl amine and cyclododecyl amine.

The reaction of the cyclic amine with epichlorohydrin is allowed to proceed in the refluxing absolute lower alkyl alcohol. It is preferred that the refluxing solvent be absolute ethanol and that the first reaction be allowed to proceed for about 24 hours to yield the epoxide hydrochloride. However, shorter reaction times such as 1-6 hours can, of course, be employed.

Then, in the second stage of the reaction, the epoxide hydrochloride is reacted with a large excess of t-butylamine in the refluxing absolute lower alkyl alcohol. The epoxide hydrochloride need not be isolated prior to the subsequent reaction with t-butylamine, although, of course, if desired, the epoxide hydrochloride may be isolated. In particular, it is preferred that about 1.1 to 3.0 moles of t-butylamine be used per mole of epoxide hydrochloride. However, it is even more preferred to use about 1.5 to about 2.5 moles of t-butylamine per mole of epoxide hydrochloride. Typically, the reaction is most advantageously conducted with about 2 moles of t-butylamine per mole of epoxide hydrochloride.

Again, it is preferable to use absolute ethanol in the second stage of reaction as the refluxing absolute lower alkyl alcohol. It is also preferred that the reflux in this stage be continued for about 24 hours. However, shorter reaction times such as about 1–6 hours can, of course, be employed.

Further, it should be noted that while absolute lower alkyl alcohols are the organic solvents of choice for the refluxing solvent in both the first and second reaction stages, it is specifically contemplated that any other organic solvent may be used as an equivalent to the absolute lower alkyl alcohols of the present invention provided that the reactants are sufficiently soluble in the solvent and that the formed epoxide does not open (i.e., cleave) prior to reaction with t-butylamine. Also, the refluxing temperature of this solvent should fall within or near the boiling point range of the lower alkyl alcohols of the present invention. For example, a lower ketone such as acetone, substantially free of water, might also be used. However, it is understood that one skilled in the art would easily be able to ascertain which organic solvents could also be used in view of the above-described properties.

In general, sufficient absolute lower alkyl alcohol should be used in both stages of the reaction to dissolve the reactants. This, of course, depends upon the amounts of the reactants being used.

The present invention will now be further illustrated by certain examples and references which are provided for purposes of illustration only and are not intended to limit the present invention.

EXAMPLE 1

1.0 mole (128.0 g) of cyclooctylamine is reacted with 1.1 moles (102.7 g) of epichlorohydrin in about 500 mls of absolute ethanol at reflux for about 24 hours to yield the hydrochloride of the epoxide having the formula:

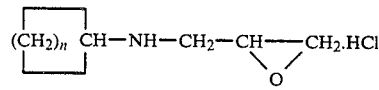

The epoxide hydrochloride is then isolated by solvent removal, and, without purification, is dissolved in about 500 mls of absolute ethanol and reacted with 2.0 moles (146.0 g) of t-butylamine in the refluxing absolute ethanol for about 24 hours.

After solvent evaporation, the product having the formula:

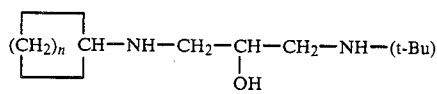

is column-purified and recrystallized. The yield of the base is about 60%. The base is then converted to the dihydrochloride salt (COR 37 07C).

The melting point of the hydrochloride is about 125° C. (with decomposition). NMR spectrum of the base: $\delta = 1.05$ ppm (1 s, 9 H; t-Bu); $\delta = 1.50$ ppm (1 m, 14 H; $(CH_2)_7$); $\delta = 2.5$ ppm (1 m, 4 H; 2 $CH_2N$); $\delta = 3.6$ ppm (1 m, 2 H; CHO+CHN).

EXAMPLE 2

The procedure of Example 1 was followed except for the fact that cyclododecylamine was used instead of cyclooctylamine, to yield 38% of the base. The base is then converted to the dihydrochloride salt (COR 37 52C).

NMR spectrum of the free base: $\delta = 1.05$ ppm (1 s, 9 H; t-Bu); $\delta = 1.3$ ppm (1 m, 22 H; $(CH_2)_{11}$); $\delta = 2.5$ ppm (1 m, 5 H; CH-N); $\delta = 3.6$ ppm (1 m, 1 H; CHO).

The toxicological and pharmacological properties of the present compounds will now be described.

The acute lethal toxicity was determined on mice. Per os, both COR37 07C and COR37 52C caused 0% mortality at 300 mg/kg. Mortalities with either compound intraperitoneally at 100 mg/kg were 0% at 200 mg/kg 100%.

The antimicrobial activity was determined in vitro by the well-known technique of dilution in tubes. The minimum inhibiting concentration (m.i.c.) for each compound was 5 ug/ml for *Staph. aureus*; for COR37 07C, the m.i.c. for *E.coli* was 5 ug/ml; and for COR37 52C, it was 20 ug/ml; for COR37 07C, the m.i.c. for *Mycobacterium ranae* was 20 ug/ml, and 20 ug/ml also for *Pseudomonas aeruginosa*; for either compound the m.i.c. for *Trichophyton mentagrophytes* was 20 ug/m; for COR37 07C, the m.i.c. for *Proteus vulgaris* was 5 ug/ml, and for COR37 52C, it was 20 ug/ml; and for COR37, the m.i.c. for *Klebsiella pneumoniae* was 5 ug/ml.

In another test carried out in vitro according to the French Standard NF T 72.151, the results with COR37 07C were as follows:

| | |
|---|---|
| *Escherichia coli*, ATCC 10536 | m.i.c. = m.b.c. = 4 μg/ml |
| *Staphylococcus aureus*, ATCC 9144 | m.i.c. = m.b.c. = 4 μg/ml |
| *Pseudomonas aeruginosa*, CNCM A 22 | m.i.c. = 128 μg/ml<br>m.b.c. = 256 μg/ml |
| *Streptococcus faecalis*, ATCC 10541 | m.i.c. = m.b.c. = 4 μg/ml |
| *Mycobacterium smegmatis*, CNCM 7326 | m.i.c. = m.b.c. = 1 μg/ml. |

Thus, the compounds of the present invention are advantageously used as antimicrobial agents. While the present compounds and, of course, compositions containing the same have excellent antimicrobial activities, they also exhibit relatively low toxicities toward the host mammal.

The present compounds have also been found to present an anticalcic activity. The activity was evaluated in vitro, by the action on the contractile force of the atrium of a guinea pig under electrical stimulation. COR37 07C at a concentration of 10 ug/ml diminished this force by more than 40%. This effect was inhibited by the addition of calcium ions.

The platelet anti-aggregation activity of the present compounds was also determined in vitro, by the action on platelet aggregation induced by $10^{-6}$ M ADP in rabbit plasma rich in platelets. COR37 07C at 25 ug/ml inhibited this aggregation by 60%; the use of adenosine at 100 ug/ml brought about 64% inhibition under the same conditions.

Aggregation induced by 0.05 ml of a standard preparation of bovine collagen in platelet-rich rabbit plasma was inhibited 100% by COR37 07C at 5 ug/ml or COR37 52C at 10 ug/ml. The addition of aspirin at 10 ug/ml (to the raw test preparation) also brought about 100% inhibition under the same conditions.

In view of the pharmacological activities described above, combined with relatively low toxicity, the compounds of the present invention may be advantageously employed in human and veterinary therapy. The antimicrobial activity of the present compounds facilitates their employment, for example, separately or in combination, as, e.g., antiseptics or disinfectants for antisepsis of hands, of healthy or injured skin, or of mucous or serous membranes, and for disinfection of materials and surfaces. They may be used as indicated in combination with the customary non-toxic excipients, in the form, e.g., of an aqueous solution of tincture, an effervescent or foaming solution, a soap, an ointment, a gynecological tablet, an ovule, or an impregnated dressing. Solutions may comprise the active principle in the amount of, e.g., 0.1 to 10%, and may also be used pure or diluted, as indicated. The gynecological forms, e.g., tablets and ovules, may comprise the active principle in the amount of, e.g., 0.050 to 0.250 g per unit of formulation. The inventive products may also be employed in the treatment of general, i.e., systemic, infections.

In view of their anticalcic effectiveness, the present compounds and compositions containing the same may be employed in the treatment of coronary insufficiency. In view of their antiaggregant properties with respect to platelets, they may be used in treatment of states of hyperaggregability of platelets. In combination with the customary pharmaceutically-acceptable excipients, the present compounds may be administered, e.g., orally in the form of coated pills, compressed tablets, syrups, or capsules, or rectally in the form of suppositories, intramuscularly, or even intravenously. Doses will vary according to the need and the patient, for example, from 1 to 100 mg/da in one to six doses p.o. or one or two doses rectally, or 0.5 to 50 mg/da by injection, for the parenteral modes.

The compounds of the present invention are preferably used as pharmaceutically-acceptable salts. Salts which may be advantageously used are the sulfate, phosphate, citrate or hydrochloride salts, for example. However, of particular use is the hydrochloride, i.e., dihydrochloride salt.

Having now fully described this invention, it will be apparent to one of ordinary skill in the art that many charges and modifications can be made thereto without departing from the spirit or scope of the invention as set forth herein.

What is claimed as new and desired to be secured by Letters Patent of the United States is:

1. A compound having the formula (I):

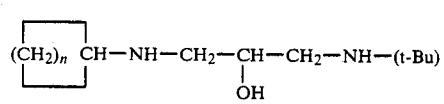

wherein n is an integer between 7 and 11, inclusive; or the pharmaceutically acceptable salts thereof.

2. The compound according to claim 1, wherein n is 7.

3. The compound according to claim 1, wherein n is 11.

4. The compound according to claim 1, wherein said pharmaceutically acceptable salt is the dihydrochloride salt.

5. The compound according to claim 1, wherein n is 8.

6. The compound according to claim 1, wherein n is 9.

7. The compound according to claim 1, wherein n is 10.

* * * * *